US008661878B2

(12) United States Patent
Henning et al.

(10) Patent No.: US 8,661,878 B2
(45) Date of Patent: Mar. 4, 2014

(54) KINEMATIC VISCOMETER AND METHOD

(75) Inventors: Patrick F. Henning, Concord, MA (US); Thomas G. Barraclough, Maynard, MA (US); Brian A. Tweed, Dracut, MA (US); Eric J. Olson, Phillipston, MA (US)

(73) Assignee: Spectro, Inc., Chelmsford, MA (US)

( * ) Notice: Subject to any disclaimer, the term of this patent is extended or adjusted under 35 U.S.C. 154(b) by 419 days.

(21) Appl. No.: 12/930,886

(22) Filed: Jan. 18, 2011

(65) Prior Publication Data

US 2012/0180553 A1 Jul. 19, 2012

(51) Int. Cl.
*G01N 11/06* (2006.01)

(52) U.S. Cl.
USPC .................................................. 73/54.07

(58) Field of Classification Search
USPC ............. 73/54.13, 54.5, 114.52, 1.73, 54.04, 73/54.07
See application file for complete search history.

(56) References Cited

U.S. PATENT DOCUMENTS

| 3,569,722 | A | * | 3/1971 | Denson | 356/632 |
|---|---|---|---|---|---|
| 4,415,941 | A | * | 11/1983 | Gibeau et al. | 360/266.5 |
| 4,554,821 | A | * | 11/1985 | Kiesewetter et al. | 73/54.07 |
| 4,596,137 | A | * | 6/1986 | Fisher et al. | 73/54.36 |
| 4,840,515 | A | * | 6/1989 | Freese | 405/45 |
| 5,383,314 | A | * | 1/1995 | Rothberg | 52/169.5 |
| 5,470,757 | A | * | 11/1995 | Gagnon et al. | 436/164 |
| 5,673,521 | A | * | 10/1997 | Coulton et al. | 52/199 |
| 5,688,073 | A | * | 11/1997 | Brodeur et al. | 405/45 |
| 5,710,374 | A | * | 1/1998 | Ross et al. | 73/54.24 |
| 5,764,355 | A | * | 6/1998 | Gagnon et al. | 356/244 |
| 5,856,870 | A | | 1/1999 | Curtiss | |
| 6,289,149 | B1 | | 9/2001 | Drury et al. | |
| 6,308,472 | B1 | * | 10/2001 | Coulton et al. | 52/198 |
| 6,322,223 | B1 | | 11/2001 | Smith et al. | |
| 6,411,434 | B1 | | 6/2002 | Eastman et al. | |
| 6,412,338 | B2 | * | 7/2002 | Boyle et al. | 73/54.34 |
| 6,561,010 | B2 | * | 5/2003 | Wilson et al. | 73/54.04 |
| 6,898,963 | B2 | * | 5/2005 | Irani | 73/54.04 |
| 6,919,654 | B2 | * | 7/2005 | Harned et al. | 310/12.01 |
| 7,131,318 | B2 | * | 11/2006 | Tsang et al. | 73/54.07 |
| 7,188,515 | B2 | * | 3/2007 | Burns et al. | 73/54.05 |
| 7,775,976 | B2 | * | 8/2010 | Fuller et al. | 600/369 |
| 8,384,895 | B2 | | 2/2013 | Albin et al. | |
| 2002/0080362 | A1 | * | 6/2002 | Behroozi | 356/477 |
| 2002/0184941 | A1 | * | 12/2002 | Shin et al. | 73/54.01 |
| 2003/0005752 | A1 | * | 1/2003 | Shin et al. | 73/54.01 |
| 2004/0007921 | A1 | * | 1/2004 | Harned et al. | 310/12 |
| 2004/0149018 | A1 | * | 8/2004 | Taylor | 73/54.22 |
| 2006/0179923 | A1 | * | 8/2006 | Burns et al. | 73/54.07 |
| 2006/0201333 | A1 | * | 9/2006 | Friel et al. | 99/372 |

(Continued)

OTHER PUBLICATIONS

Written opinion of the International Searching Authority for International Application No. PCT/US2011/001991, Apr. 20, 2012, eight (8) pages, unnumbered.

*Primary Examiner* — John Fitzgerald
(74) *Attorney, Agent, or Firm* — Iandiorio Teska & Coleman, LLP (57) ABSTRACT

A viscometer assembly includes a first plate with a rail configured to constrain fluid thereon between its edges by surface tension. A second opposing plate has a surface spaced from the rail by a predefined gap of constraining fluid to the rail by surface tension when the rail is inclined and gravity pulls the fluid along the rail. The kinematic viscosity of the fluid is determined as a function of the predetermined gap and the time it takes the fluid to flow along the rail.

32 Claims, 5 Drawing Sheets

(56) References Cited

U.S. PATENT DOCUMENTS

| | | |
|---|---|---|
| 2007/0105185 A1* | 5/2007 | Cima et al. ............... 435/33 |
| 2007/0121113 A1 | 5/2007 | Cohen et al. |
| 2007/0182961 A1 | 8/2007 | Chadha et al. |
| 2007/0227234 A1* | 10/2007 | Weisinger ............... 73/54.13 |
| 2007/0277678 A1* | 12/2007 | Mangano ............... 99/426 |
| 2008/0186351 A1* | 8/2008 | Takahashi ............... 347/19 |
| 2009/0025570 A1* | 1/2009 | Larson ............... 99/376 |

* cited by examiner

KINEMATIC VISCOMETER AND METHOD

FIELD OF THE INVENTION

The subject invention relates to viscosity measurement and a viscometer useful for measuring the viscosity of a fluid such as oil.

BACKGROUND OF THE INVENTION

Existing viscometers fall into several classes. Field viscometers typically have no temperature control, require solvents or disposables, can only measure absolute viscosity (not the desired kinematic viscosity for many applications), can be inaccurate, and may require significant mechanical actions on the part of the user. Acoustic wave field viscometers typically operate over wide (very high) shear rates that do not correspond in many cases to laboratory readings. On the other hand, both of these first two types of viscometers can be made to operate under extreme conditions such as high temperature and pressure and can provide value for targeted systems where a single process is being monitored, for example. The third class of viscometers are traditional laboratory viscometers which fall sub-classes such as the following: capillary, rotating, piston and orifice. All of these viscometers are high-cost and/or require extensive care when using them, and many may not be suitable for field use.

BRIEF SUMMARY OF THE INVENTION

In various aspects, the invention provides, in one example, a kinematic viscometer designed for field use and which is easy to clean, is inexpensive, accurate, does not typically require the use of solvents, provides temperature control, and can be made small and lightweight.

The subject invention results, at least in part, from the realization that, in one particular example, by constraining a fluid sample to flow under the force of gravity on a rail in a gap between the rail and a surface over the rail, the kinematic viscosity of the sample is now a function of the gap and the velocity of the sample which can be determined by measuring the time it takes for the sample to traverse two defined locations along the rail.

The subject invention, however, in other embodiments, need not achieve all these objectives and the claims hereof should not be limited to structures or methods capable of achieving these objectives.

The subject invention features a viscometer comprising a first plate including a rail configured to constrain fluid thereon between its edges by surface tension and a second opposing plate including a surface spaced from the rail by a predefined gap for constraining fluid to the rail by surface tension when the rail is inclined and gravity pulls the fluid along the rail. There are means for determining the kinematic viscosity of the fluid as a function of the predetermined gap and the time it takes the fluid to flow along the rail such as spaced sources directing electromagnetic energy into the gap and a corresponding set of spaced electromagnetic energy detectors.

Preferably, at least one of the first plate and the second plate includes kinematic mounts providing the predefined gap one or both of the plates include at least one magnet for releasably coupling the plates together. The first plate typically includes raised lands spaced from and on opposite sides of the rail. Typically, the magnets are associated with select lands and the kinematic mounts associated with select lands. The lands can be spaced from each other defining channels between the lands transverse to the rail for monitoring the time it takes fluid to flow along the rail.

The rail typically has a proximal end defining a well. In one version, the well includes a ramp sloping up to the rail and the rail divides into split fingers on opposite sides of the ramp. The second plate may also includes a ramp. A heater associated with at least one plate may also be provided.

In one aspect, a viscometer assembly in accordance with the invention features a first plate including a rail, a second opposing plate, and devices or features providing a predefined gap between the rail and the second plate. Kinematic mounts may be used.

A viscometer in accordance with an example of the invention features a first member including a rail, a second opposing member including a surface spaced over the rail by a predefined gap, kinematic mounts associated with one or both members for spacing said surface of said second member over the rail by the gap, and one or more magnets associated with one or both members for releasably coupling the members together.

In one aspect, a viscometer includes a first member with a rail configured to constrain a fluid thereon between its edges by surface tension and raised lands spaced from and on opposite sides of the rail wherein the lands are spaced from each other defining channels between the lands transversed to the rail for determining the amount of time that it takes fluid to flow along the rail. A second opposing member includes a surface spaced from the rail of the first member by a gap for constraining fluid to the rail by surface tension when the rail is inclined and gravity pulls the fluid along the rail. One or more magnets are associated with the one or both members and one or more mounts are associated with one or both members for defining the gap.

The invention also features a method of determining the kinematic viscosity of a fluid. One preferred method comprises constraining a sample of the fluid to flow in a gap between a rail and a surface spaced from the rail measuring the time it takes the fluid sample to flow between two defined locations on the rail determining, based on the time, the velocity of the fluid sample and based on the velocity, calculating the kinematic viscosity of the fluid sample typically by using an equation wherein the kinematic viscosity is a function of the gap and the velocity.

One method of determining the kinematic viscosity of a fluid features constraining a sample of the fluid to flow in a gap between a rail and a surface over the rail determining the velocity of the fluid sample as it flows along the rail and based on the velocity, calculating the kinematic viscosity of the fluid sample.

Determining the velocity may include measuring the time it takes the fluid sample to flow between two defined locations on the rail and calculating the kinematic viscosity of the fluid sample includes using an equation wherein the kinematic velocity is a function of the gap and the velocity.

The invention also features a method of manufacturing a viscometer including a rail configured to constrain fluid thereon between its edges by surface tension and providing a surface spaced from the rail by a predefined gap for constraining fluid to the rail by surface tension when the rail is inclined and gravity pulls the fluid along the rail. The two plates are releasably coupled together so that the plates can be separated in order to clean the rail.

The method may also include adding kinematic mounts to one and/or both plates providing the predefined gap and providing at least one magnet for releasably coupling the plates together. The method may also include forming raised lands spaced from and on opposite sides of the rail.

A well can be provided adjacent the rail and the rail can be divided on opposite sides of a ramp defining the well. A heater associated with at least one plate can also be provided.

BRIEF DESCRIPTION OF THE SEVERAL VIEWS OF THE DRAWINGS

Other objects, features and advantages will occur to those skilled in the art from the following description of a preferred embodiment and the accompanying drawings, in which.

DETAILED DESCRIPTION OF THE INVENTION

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings. If only one embodiment is described herein, the claims hereof are not to be limited to that embodiment. Moreover, the claims hereof are not to be read restrictively unless there is clear and convincing evidence manifesting a certain exclusion, restriction, or disclaimer.

A unique kinematic viscometer in accordance with the invention makes use of a phenomena of immobilizing two physical dimensions so that the fluid mechanics of the system are dictated by one well-controlled dimension. In this way, the Naivier-Stokes equation describing fluid flow reduces to a remarkably simple form relating fluid kinematic viscosity to well-defined parameters in addition to measuring velocity of the fluid in one dimension. If this dimension is well-controlled, it allows for remarkably accurate forms for viscosity measurement with small to non-existent correction factors for the actual device needed. Further, the device can be solvent-free with only the need to load the sample and wipe it off with a rag once the measurement is complete. Device accuracy and precision is comparable to other commercial viscometers but at a significantly lower cost and with no need for consumables. Finally, the device only requires microliters of fluid for operation.

One aspect of the invention is to address the need for kinematic viscometers which are not bulky, such as requiring temperature baths, solvents, pumps, etc. as are commonly encountered in the laboratory. In addition, the new viscometer can be temperature-controlled, used in the field, and provide reasonable accuracy. Finally, a viscometer which requires no consumables and can be cleaned with only the wipe of a rag would eliminate most of the issues encountered when considering field or portable viscometers.

The invention makes use of the kinematic mounting concepts allowing two plates to be held in close proximity with sub-micron accuracy. On one of the plates, a groove channel pattern is cut such that a fluid performs a guided flow when prompted by gravity down the channel. The fluid is placed in a reservoir area at the top of the plate, the two plates are closed, and the fluid begins flowing into the channel from the reservoir. By visual inspection (or via position sensors), the flow of the fluid down the channel can be observed and recorded. If the velocity of the fluid is measured in this way, the kinematic viscosity can be calculated.

With guide gulleys on either side of the flow path, the fluid is prevented by surface tension from having any movement outside the channel and thus no flow takes place in the channel direction. Further, when the second plate, with well-defined spacing, is placed on top of the plate containing fluid, the fluid encounters surface tension with this narrow restriction which, along with the gravitational force pulling the fluid down the channel, dictates the fluid's velocity and thus allows viscosity to be calculated.

By using laser diodes and very low-cost detectors, in one example, the position of the fluid may be monitored by aligning the laser through the plates at various defined points with the detectors receiving the radiation mounted on the other side of the plates. If the distance between these points are known, the velocity of the fluid may be calculated from observation and used to determine kinematic viscosity.

The as-built device has demonstrated operation and good accuracy and precision between 10-400 centiStokes at room temperature or controlled at 40° C.

The result is the first known wipe-clean kinematic viscometer, a solvent-free kinematic viscometer, a miniature capillary viscometer, and the use of one-dimensional fluid flow to obtain viscosity and to minimize viscosity estimation caculational errors and need for large correction factors. There is the possibility of ultimate integration to an infrared/optical fluid cell so that two measurements may be performed with one fixture. Well-defined, wide laser spots can be used so that the liquid "bulb" which is typically encountered at fluid-flow front and can introduce errors into a velocity measurement is averted and a position indication is only indicated when the beam is fully suppressed when the fluid flow encounters. Multiple laser position sensors can be used so that a single device may encounter a wide range of sample viscosities. A rapid thermal stabilization of the liquid under test is possible due to the extremely small (microliter level) amount of fluid analyzed. Fluid calibration checks can be simplified.

Figure 1:
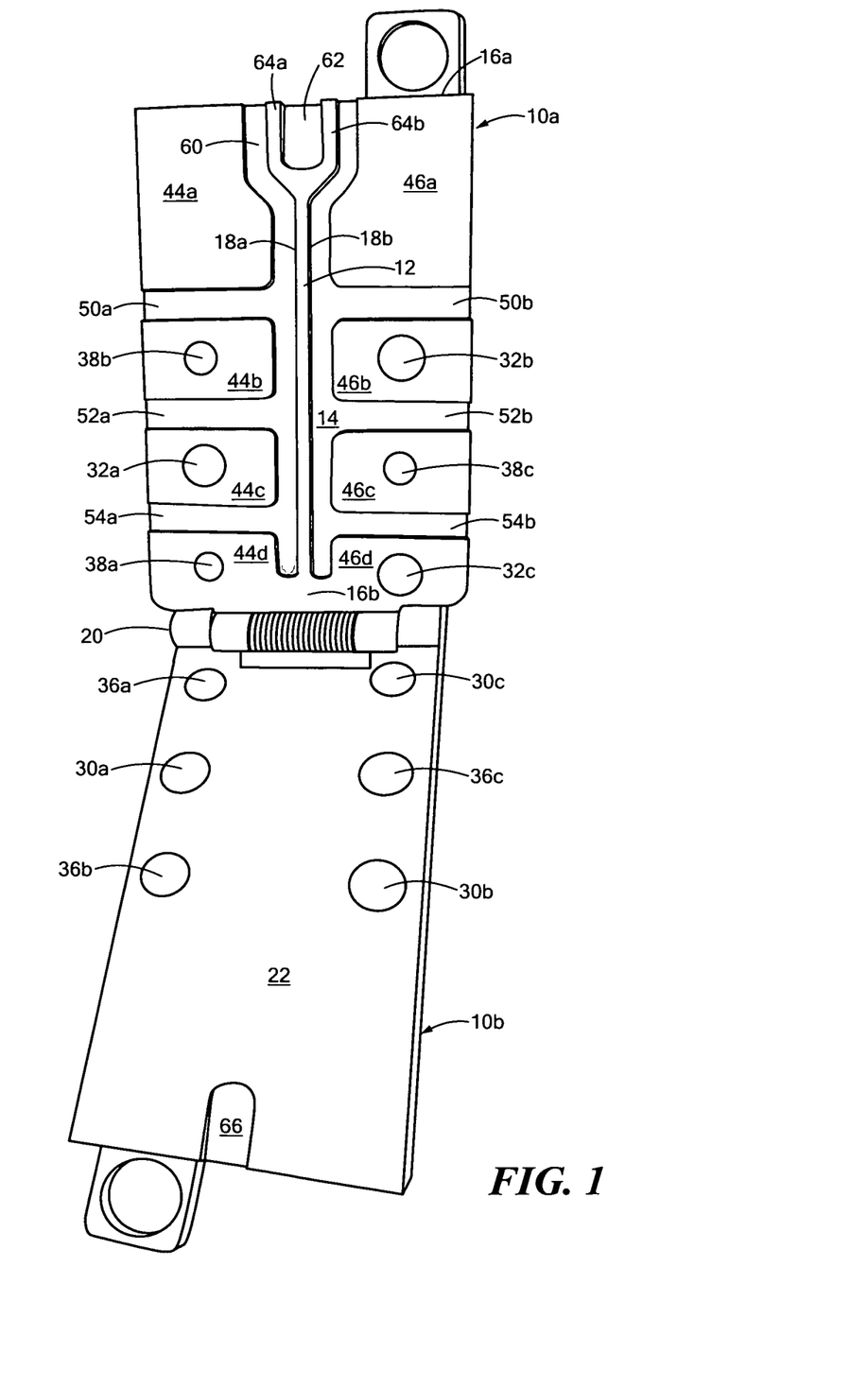
FIG. 1 is a schematic three-dimensional view showing one example of a kinematic viscometer in accordance with the invention.

In one particular example as described in FIG. 1, a kinematic viscometer in accordance with the invention features first plate 10$a$ with at least one rail 12 thereon raised from plate floor 14 and extending from proximal (e.g., top) end 16$a$ to distal (e.g., bottom) end 16$b$. Rail 12 in one prototype example was 918 μm in width, between 0.01 and 0.02 inches high, and between 2 and 3 inches long. The top surface of rail 12 was flat to 16 RMS and +/1 degree. Rail 12 is thus configured to constrain a fluid thereon between edges 18$a$ and 18$b$ of the rail by surface tension.

Second plate 10$b$ is typically hinged to plate 10$a$ as shown at 20 and includes flat surface 22 to 16 RMS and +/1 degree over rail 12 separated therefrom by a predetermined gap (e.g., 100-200 μm) and thus constrains fluid to the rail by surface tension when rail 12 (and plate 10$a$) is inclined (e.g., positioned vertically) and gravity pulls fluid along the rail from proximal end 16$a$ to distal end 16$b$. Typically, the gap is much less than 9 times the width of the rail.

In this particular design, plate 10$b$ includes spaced recessed positive face magnets 30$a$, 30$b$, and 30$c$ and plate 10$a$ includes corresponding negative face magnets 32$a$, 32$b$, and 32$c$ received in raised flat lands 44$c$, 46$b$, and 46$d$, respectively. Lands 44$c$, 46$b$, and 46$d$ may be the same height as rail 12. Magnets 30 and 32 releasably couple plate 10a to plate 10b in order for plates 10a and 10b to be used for viscosity measurements and then separated (via the hinge) for cleaning. Alternatively, items 30a-30c could be magnets and items 32a-32c could be ferromagnetic material. The relative position of the magnets and/or the ferromagnetic material in the respective plates could also be reversed.

To properly space surface 22 of plate 10b over rail 12 by a specific (e.g., 100 μm) gap when the two plates are coupled together, kinematic mounts 36a-36c are disposed in plate 10b as shown and mate with disks 38a-38c, respectively. Disk 38a-38c are disposed flush in lands 44d, 44b, and 46c, respectively, which also typically have a height the same as the height of rail 12. The same is true for lands 44a and 46a. Other means for providing a predefined gap between the top surface of rail 12 and plate 10b, however, are within the scope of the subject invention. See also U.S. Patent Application Publication No. 2010/0182599 incorporated herein by this reference.

As shown, lands 44a-44d are spaced from each other and they are also spaced from rail 12 on one side of rail 12 while lands 46a-46d are spaced from rail 12 on the opposite side of rail 12. This arrangement, in turn, defines cross wise channels 50a and 50b, 52a and 52b, and 54a and 54b. Electromagnetic energy (e.g., laser light or LED light) can be directed in these channels in order to measure the velocity of a fluid sample moving along rail 12 as discussed below.

In this particular embodiment, rail 12 also has proximal end 60 defining a well with ramp 62 sloping upwards to the rail top surface. Rail 12 divides into split fingers 64a and 64b on opposite sides of ramp 62. Ramp 66 may also be provided in plate 10b as shown to further define the fluid sample well. Various materials may be used for plates 10a and 10b including aluminum and stainless steel and typically all the features shown are machined or otherwise formed on the surfaces of the respective plates.

Figure 2A:
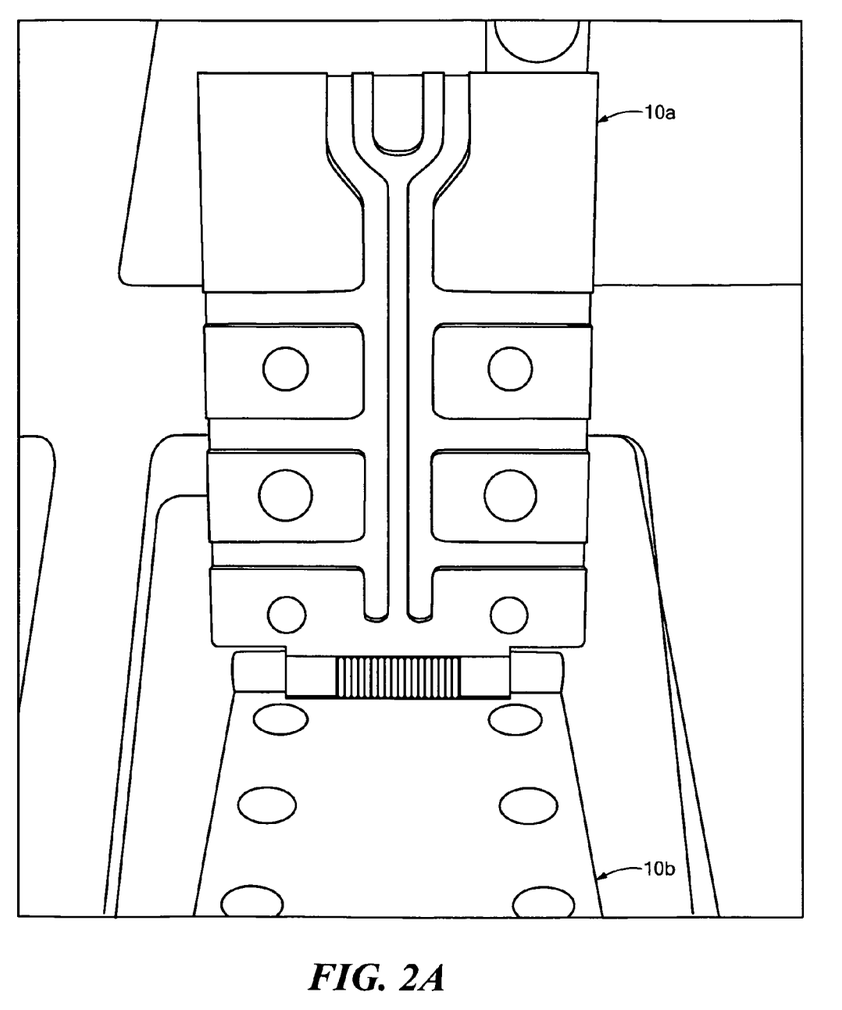
FIGS. 2A-2C are schematic views showing the two plates of the viscometer of FIG. 1 being folded up together and inserted into an analysis unit in accordance with an example of the invention.
Figure 2B:
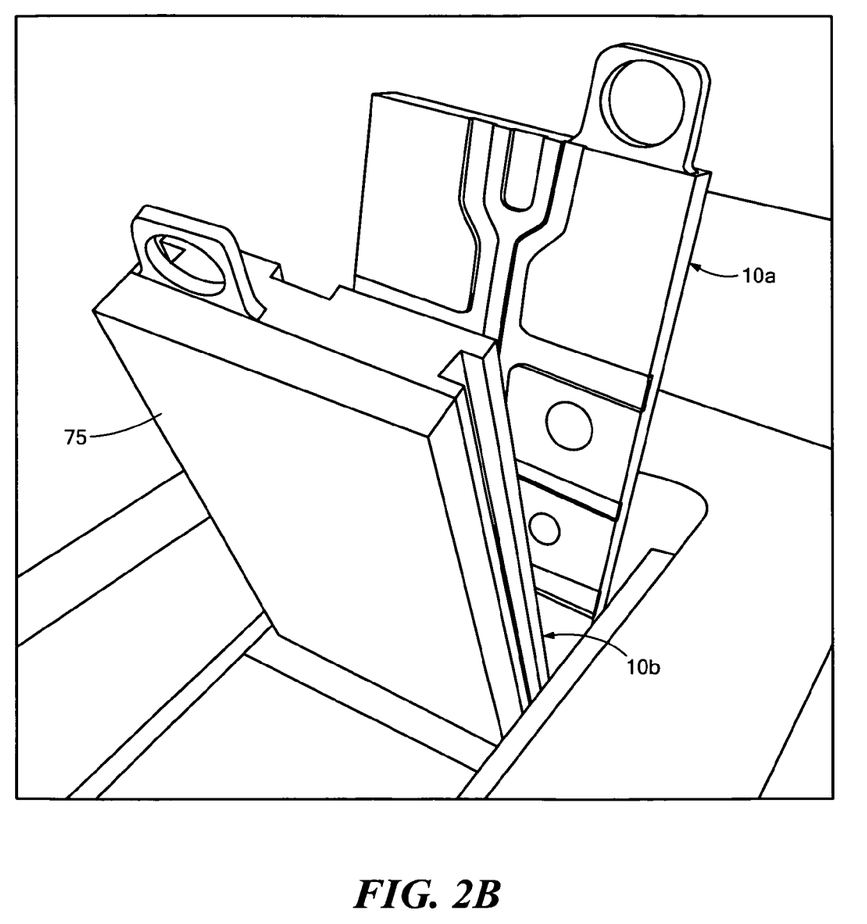
Figure 2C:
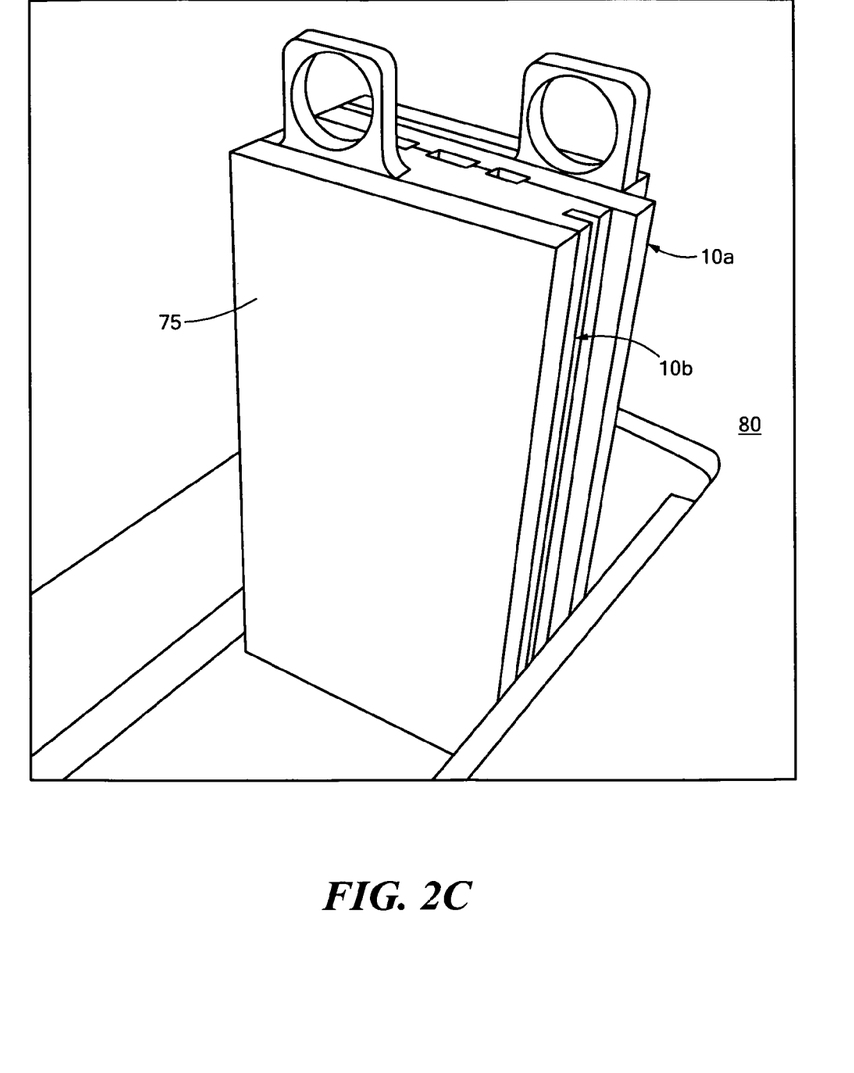

FIGS. 2A-2C show plates 10a and 10b being folded up into a coupled relationship where rail 12, FIG. 1 is now oriented vertically and plate 10b is releasably coupled to plate 10a via magnets 30a-30c and 32a-32c and surface 22 of plate 10b is spaced by a predefined gap over the top surface of rail 12 by kinematic mounts 36a-36b. Once plates 10a and 10b are vertically disposed as shown in FIG. 2C, they are driven downward into analysis unit 80. FIGS. 2B and 2C also show heater element 75 on the rearward surface of plate 10b for heating the sample to a predefined temperature, for example 40° C.

Figure 3:
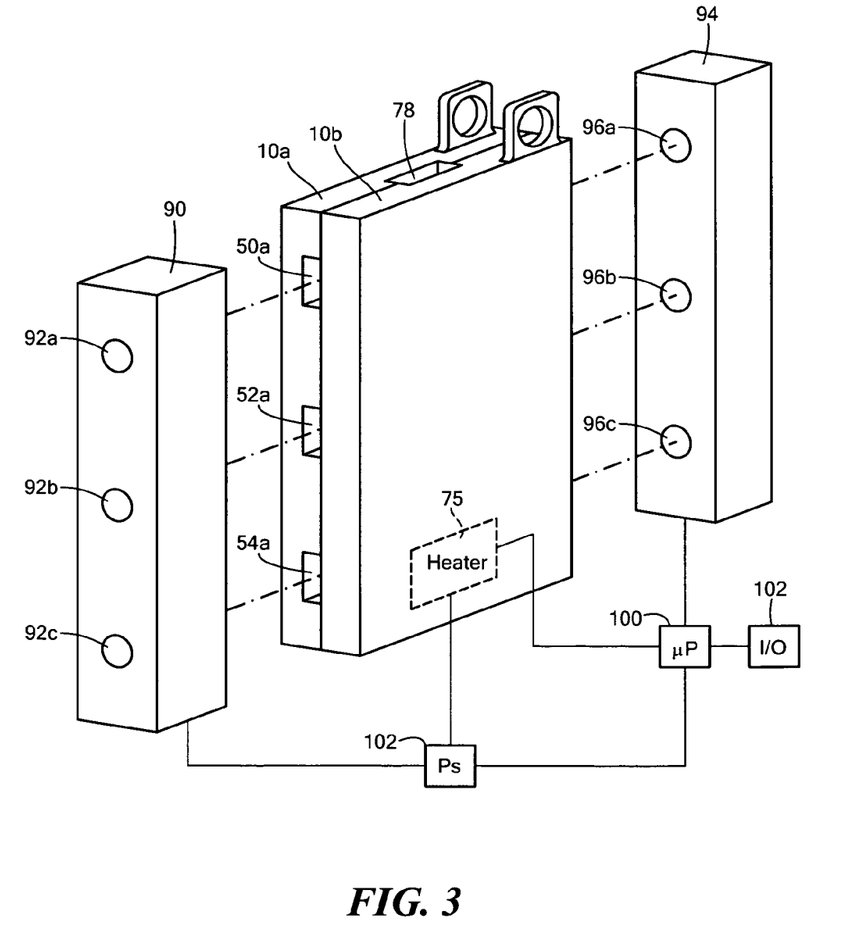
FIG. 3 is a highly schematic view showing the primary components associated with an example of a kinematic viscometer in accordance with an example of the subject invention.

FIG. 3 depicts plates 10a and 10b coupled together and vertically disposed within the analysis unit which typically includes sources of electromagnetic radiation as shown at 90 with LEDs 92a, 92b, and 92c on one side of releasably coupled together plates 10a and 10b and detector assembly 94 with corresponding detector elements 96a, 96b, and 96c on an opposite side of plates 10a, 10b.

This arrangement allows for a measurement of the time it takes fluid on the top surface of rail 12a to move along rail 12 in order to thus provide a calculation of the velocity of the fluid on rail 12.

Sources 92 direct light through the gap between the rail and the surface spaced from the rail. A sample of a fluid is deposited at well 78 (defined by sloping ramp 62a in plate 10a and sloping ramp 66 in plate 10b, FIG. 1). The sample may be oil from an engine crank case or the like. The sample begins to flow under the force of gravity along rail 12, FIG. 1 and is constrained to the top surface of rail 12 via the design of rail 12 itself and the gap between rail 12 and surface 22 of plate 10b. LEDs 92a, 92b, and 92c, FIG. 3 direct light in channels 50a, 52a, and 54a, respectively, as shown. For example, the light from LED 92a is directed in channel 50a, FIG. 1, through the gap between the top of rail 12 and surface 22 of plate 10b, and then to channel 50b to be detected by detector 96a, FIG. 3. Light from LED 92b, in turn, is directed into channel 52a, FIG. 1, through the gap between the top of rail 12 and surface 22 of plate 10b, and then through channel 52b to be detected by detector 96b, FIG. 3. Similarly, light from LED 92c is directed into channel 54a, through the gap between the top of rail 12 and surface 22 of plate 10b, and then through channel 54b to be detected by detector 96c. The distance between the channels 50a, 52a, and 54a and/or the LEDs, and the like are known and thus, by using detectors 96a, 96b, and 96c, the time it takes the sample fluid to traverse known locations on rail 12 can be determined since detectors 96a, 96b, and 96c will no longer output a signal (or will output a different signal) indicating that they are detecting light from LED sources 92a, 92b, and 92c, respectively, when the oil on rail 12, FIG. 1 blocks or diffuses the light transmitted by the LED sources. Other sources of electromagnetic radiation can also be used including lasers.

Microprocessor or controller 100 operates heater 75 via power source 102, and also, based on commands from input/output section 102 energizes the LEDs of transmitter 90 and reads the output from detector array 94 in order to calculate the velocity of the fluid moving in the gap between rail 12 and surface 22 of plate 10b, FIG. 1. Microprocessor or controller 100 then preferably uses the velocity to determine the kinematic viscosity according to the equation:

$$\text{Kinematic viscosity} = \text{gap thickness} * K * \text{accelerated due to gravity} * \frac{1}{\text{velocity}} \quad (1)$$

The gap is known (e.g., 100 μm), as is the constant $K$ $\left(\text{e.g.} \frac{1}{6}\right)$, and the acceleration due to gravity. Other means for determining the kinematic viscosity of the fluid as a function of the predefined gap between the rail and surface 22 of plate 10b and the time it takes the fluid to flow along the rail are also within the scope of the subject invention. Microprocessor 100 can be programmed as set forth above and may reside in a portable computer of the like. The plates are then separated, the rail wiped clean, and then the viscometer is ready again for use.

Although specific features of the invention are shown in some drawings and not in others, however, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments.

In addition, any amendment presented during the prosecution of the patent application for this patent is not a disclaimer of any claim element presented in the application as filed: those skilled in the art cannot reasonably be expected to draft a claim that would literally encompass all possible equivalents, many equivalents will be unforeseeable at the time of the amendment and are beyond a fair interpretation of what is to be surrendered (if anything), the rationale underlying the amendment may bear no more than a tangential relation to many equivalents, and/or there are many other reasons the applicant can not be expected to describe certain insubstantial substitutes for any claim element amended.

Other embodiments will occur to those skilled in the art and are within the following claims.

The invention claimed is:

1. A viscometer comprising:
   a first plate including a rail configured to constrain fluid thereon between its edges by surface tension;
   a second opposing plate including a surface spaced from the rail by a predefined gap for constraining fluid to the rail by surface tension when the rail is inclined and gravity pulls the fluid along the rail; and
   means for determining the kinematic viscosity of the fluid as a function of the predetermined gap and the time it takes the fluid to flow along the rail.

2. The viscometer of claim 1 in which said means for determining the kinematic viscosity includes spaced sources directing electromagnetic energy into the gap and a corresponding set of spaced electromagnetic energy detectors.

3. The viscometer of claim 1 in which at least one of the first plate and the second plate includes kinematic mounts providing the predefined gap.

4. The viscometer of claim 1 in which one or both of said plates include at least one magnet for releasably coupling the plates together.

5. The viscometer of claim 1 further including a heater associated with at least one said plate.

6. The viscometer of claim 1 in which the first plate includes raised lands spaced from and on opposite sides of the rail.

7. The viscometer of claim 6 further including a magnet associated with one or more raised lands and kinematic mounts associated with one or more raised lands.

8. The viscometer of claim 6 in which the lands are spaced from each other defining channels between the lands transverse to the rail for monitoring the time it takes fluid to flow along the rail.

9. The viscometer of claim 1 in which the rail has a proximal end defining a well.

10. The viscometer of claim 9 in which the second plate also includes a ramp.

11. The viscometer of claim 9 in which the well includes a ramp sloping up to the rail.

12. The viscometer of claim 11 in which the rail divides into split fingers on opposite sides of the ramp.

13. A viscometer assembly comprising:
    a first plate including a rail;
    a second opposing plate; and
    one of the first plate and the second plate including devices or features providing a predefined gap between the rail and the second plate, and one or both of said plates including at least one magnet for releasably coupling the plates together.

14. The viscometer of claim 13 further including a heater associated with at least one said plate.

15. The viscometer of claim 13 in which the first plate includes raised lands spaced from and on opposite sides of the rail.

16. The viscometer of claim 15 further including a magnet associated with one or more raised lands and kinematic mounts associated with one or more raised lands.

17. The viscometer of claim 15 in which the lands are spaced from each other defining channels between the lands transverse to the rail.

18. The viscometer of claim 13 in which the rail has a proximal end defining a well.

19. The viscometer of claim 18 in which the well includes a ramp sloping up to the rail.

20. The viscometer of claim 19 in which the rail divides into split fingers on opposite sides of the ramp.

21. The viscometer of claim 19 in which the second plate also includes a ramp.

22. A viscometer comprising:
    a first member including a rail;
    a second opposing member including a surface spaced over the rail by a predefined gap;
    kinematic mounts associated with one or both members for spacing said surface of said second member over the rail by said predetermined gap; and
    one or more magnets associated with one or both members for releasably coupling the members together.

23. The viscometer of claim 22 in which the rail has a proximal end defining a well.

24. The viscometer of claim 22 further including a heater.

25. The viscometer of claim 22 including means for determining the kinematic velocity of a fluid as a function of the predetermined gap and the time it takes the fluid to flow along the rail.

26. The viscometer of claim 25 in which said means for determining the kinematic viscosity includes spaced sources of electromagnetic energy and a corresponding set of spaced electromagnetic energy detectors.

27. A viscometer comprising:
    a first member including:
    a rail configured to constrain a fluid thereon between its edges by surface tension,
    raised lands spaced from and on opposite sides of the rail, said lands spaced from each other defining channels between the lands transversed to the rail for determining the amount of time that it takes fluid to flow along the rail;
    a second opposing member including a surface spaced from the rail of the first member by a predefined gap for constraining fluid to the rail by surface tension when the rail is inclined and gravity pulls the fluid along the rail;
    one or more magnets associated with one or both members; and
    one or more mounts associated with one or both members for setting said gap.

28. The viscometer of claim 27 in which the rail has a proximal end defining a well.

29. The viscometer of claim 27 further including a heater.

30. The viscometer of claim 27 further including means for determining the kinematic viscosity of the fluid as a function of the gap and the time it takes the fluid to flow along the rail.

31. The viscometer of claim 30 in which said means includes spaced sources of electromagnetic energy and a corresponding set of spaced detectors.

32. A viscometer assembly comprising:
    a first plate including a rail, said rail having a proximal end defining a well;
    a second opposing plate; and
    one of the first plate and the second plate including devices or features providing a predefined gap between the rail and the second plate.

* * * * *